(12) United States Patent
Wang et al.

(10) Patent No.: US 8,629,104 B2
(45) Date of Patent: Jan. 14, 2014

(54) G-CSF AND WATER-SOLUBLE POLYMER CONJUGATE

(75) Inventors: Ruijun Wang, Jiangsu (CN); Changan Sun, Jiangsu (CN); Tao Jiang, Jiangsu (CN); Wang Yali, Ontario (CA)

(73) Assignee: Jiangsu Hengrui Medicine Co. Ltd., Lianyungang, Jiangsu (CN)

( * ) Notice: Subject to any disclaimer, the term of this patent is extended or adjusted under 35 U.S.C. 154(b) by 639 days.

(21) Appl. No.: 12/918,280

(22) PCT Filed: Feb. 18, 2008

(86) PCT No.: PCT/CN2008/070320
§ 371 (c)(1),
(2), (4) Date: Aug. 18, 2010

(87) PCT Pub. No.: WO2009/103199
PCT Pub. Date: Aug. 27, 2009

(65) Prior Publication Data
US 2013/0109623 A1    May 2, 2013

(51) Int. Cl.
*A61K 38/00* (2006.01)
*A61K 38/19* (2006.01)
*A61P 7/06* (2006.01)

(52) U.S. Cl.
USPC ............................. 514/7.9; 514/1.1; 424/85.1

(58) Field of Classification Search
None
See application file for complete search history.

(56) References Cited

U.S. PATENT DOCUMENTS

| | | | |
|---|---|---|---|
| 4,904,584 A | 2/1990 | Shaw | 435/69.4 |
| 5,214,132 A | 5/1993 | Kuga et al. | 530/351 |
| 5,362,853 A | 11/1994 | Kuga et al. | 530/351 |
| 5,581,476 A | 12/1996 | Osslund | 364/496 |
| 5,824,778 A | 10/1998 | Ishikawa et al. | 530/351 |
| 5,824,784 A | 10/1998 | Kinstler et al. | 530/399 |
| 5,985,265 A | 11/1999 | Kinstler et al. | 424/85.4 |

FOREIGN PATENT DOCUMENTS

| | | | |
|---|---|---|---|
| CN | 101172161 A | 5/2008 | |
| EP | 0 335 423 | 10/1989 | ............... C07K 3/08 |
| EP | 0 401 384 | 12/1990 | ............. C07K 13/00 |
| WO | WO 00/44785 | 8/2000 | ........... C07K 14/535 |
| WO | WO 01/51510 A2 | 7/2001 | ............. C07K 14/00 |
| WO | WO 2006/063055 A2 | 6/2006 | .............. C12S 13/00 |
| WO | WO 2006/135176 A1 | 12/2006 | ............. A61K 47/48 |
| WO | WO 2007/019331 A2 | 2/2007 | ............. A61K 47/48 |

OTHER PUBLICATIONS

Yan et al., Mobilization of Long-Term Hematopoietic Reconstituting Cells in Mice by the Combination of Stem Cell Factor Plus Granulocyte Colony-Stimulating Factor, Blood, vol. 84, No. 3, Aug. 1, 1994, pp. 795-799.
Bensinger et al., Autologous Transplantation With Peripheral Blood Mononuclear Cells Collected After Administration of Recombinant Granulocyte Stimulating Factor, Blood, vol. 81, No. 11, Jun. 1, 1993, pp. 3158-3163.
Neben et al., Mobilization of Hematopoietic Stem and Progenitor Cell Subpopulations From the Marrow to the Blood of Mice Following Cyclophosphamide and/or Granulocyte Colony-Stimulating Factor, Blood, vol. 81, No. 7, Apr. 1, 1993, pp. 1960-1967.
Kartre, The conjugation of proteins with polyethylene glycol and other polymers—Altering properties of proteins to enhance their therapeutic potential, Advanced Drug Delivery Reviews, 10 (1993), pp. 91-114.
Inada et al., Polyethylene Glycol(PEG)-Protein Conjugates: Application to Biomedical and Biotechnological Processes, Journal of Bioactive and Compatible Polymers, vol. 5—Jul. 1990, pp. 343-364.
Metcalf, The Molecular Biology and Functions of the Granulocyte-Macrophage Colony-Stimulating Factors, Blood, vol. 67, No. 2, Feb. 1986, pp. 257-267.

*Primary Examiner* — Gyan Chandra
(74) *Attorney, Agent, or Firm* — Brinks Gilson & Lione; Ryan L. Marshall

(57) ABSTRACT

Provided are a G-CSF and water-soluble polymer conjugate, or a pharmaceutically acceptable salt thereof, comprising a water-soluble polymer, a protein, and a linking group; a method for preparing thereof; and a pharmaceutical composition comprising the same.

35 Claims, 5 Drawing Sheets

SEQUENCE LISTING

<160> NUMBER OF SEQ ID NOS: 10

<210> SEQ ID NO 1
<211> LENGTH: 175
<212> TYPE: PRT
<213> ORGANISM: Artificial Sequence
<220> FEATURE:
<223> OTHER INFORMATION: Escherichia coli

<400> SEQUENCE: 1

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 2
<211> LENGTH: 174
<212> TYPE: PRT
<213> ORGANISM: Artificial Sequence
<220> FEATURE:
<223> OTHER INFORMATION: Escherichia coli

<400> SEQUENCE: 2

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

```
Ala Leu Gln Pro Thr Gln Gly Ala Met Pro Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 3
<211> LENGTH: 175
<212> TYPE: PRT
<213> ORGANISM: Artificial Sequence
<220> FEATURE:
<223> OTHER INFORMATION: Escherichia coli

<400> SEQUENCE: 3

```
Met Thr Pro Leu Gly Pro Ala Ser Ser Leu Pro Gln Ser Phe Leu Leu
1               5                   10                  15

Lys Ser Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 4
<211> LENGTH: 174
<212> TYPE: PRT
<213> ORGANISM: Artificial Sequence
<220> FEATURE:
<223> OTHER INFORMATION: Escherichia coli

<400> SEQUENCE: 4

```
Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95
```

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 5
<211> LENGTH: 175
<212> TYPE: PRT
<213> ORGANISM: Artificial Sequence
<220> FEATURE:
<223> OTHER INFORMATION: Escherichia coli

<400> SEQUENCE: 5

Trp Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 6
<211> LENGTH: 175
<212> TYPE: PRT
<213> ORGANISM: Artificial Sequence
<220> FEATURE:
<223> OTHER INFORMATION: Escherichia coli

<400> SEQUENCE: 6

Trp Thr Pro Leu Gly Pro Ala Ser Ser Leu Pro Gln Ser Phe Leu Leu
1               5                   10                  15

Lys Ser Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 7
<211> LENGTH: 175
<212> TYPE: PRT
<213> ORGANISM: Artificial Sequence
<220> FEATURE:
<223> OTHER INFORMATION: Escherichia coli

<400> SEQUENCE: 7

Asp Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 8
<211> LENGTH: 175
<212> TYPE: PRT
<213> ORGANISM: Artificial Sequence
<220> FEATURE:
<223> OTHER INFORMATION: Escherichia coli

<400> SEQUENCE: 8

Asp Thr Pro Leu Gly Pro Ala Ser Ser Leu Pro Gln Ser Phe Leu Leu
1               5                   10                  15

Lys Ser Leu Glu Gln Val Arg Lys Ile Gln Gly Asp Gly Ala Ala Leu
                20                  25                  30

```
Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
 50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 9
<211> LENGTH: 175
<212> TYPE: PRT
<213> ORGANISM: Artificial Sequence
<220> FEATURE:
<223> OTHER INFORMATION: Escherichia coli

<400> SEQUENCE: 9

Glu Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
 50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 10
<211> LENGTH: 175
<212> TYPE: PRT
<213> ORGANISM: Artificial Sequence
<220> FEATURE:
<223> OTHER INFORMATION: Escherichia coli

<400> SEQUENCE: 10
```

```
Glu Thr Pro Leu Gly Pro Ala Ser Ser Leu Pro Gln Ser Phe Leu Leu
1               5                   10                  15

Lys Ser Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
            85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

G-CSF AND WATER-SOLUBLE POLYMER CONJUGATE

The present application is the national phase application of PCT Application No. PCT/CN2008/070320, filed Feb. 18, 2008, the entirety of which is hereby incorporated by reference.

FIELD

This invention relates to a G-CSF conjugate modified by a water-soluble polymer having formula (I): (water-soluble polymer)–(linking group)–(N-terminus of G-CSF), or pharmaceutically acceptable salts thereof, a method for preparing the same, and a pharmaceutical composition comprising the same.

BACKGROUND

Granulocyte colony stimulating factor (G-CSF) is produced by mononuclear cells and fibroblast cells. It can stimulate granulocyte to form colonies, and has a stimulating effect on neutrophils. By combining with membrane receptors of the target cells, G-CSF mainly stimulates hematopoiesis of granulocyte and also promotes multipotent hematopoietic stem cells to enter the cell cycle; promotes proliferation, differentiation and maturation of myeloid hematopoietic progenitors; and drives the release of neutrophils into the blood. Meanwhile, it increases the number of peripheral neutrophils and improves their functions, such as phagocytosis, antibody-dependent cellular cytotoxic activity against tumor cells, etc. [Metcalf, Blood 67:257 (1986); Yan et. al., Blood 84(3): 795-799 (1994); Bensinger, et. al., Blood 81(11): 3158-3163 (1993); Neben, et. al., Blood 81(7): 1960-1967 (1993)]. Therefore, recombinant granulocyte colony stimulating factor is commonly used in cancer patients subjected to radiotherapy or chemotherapy, and leukemia patients after bone marrow transplantations as an adjuvant treatment.

Human G-CSFs commonly used on the market are Neupogen and Neutrogin, and a human G-CSF derivative, i.e. Neuwp. G-CSF derivatives or their variant proteins have also been reported in a large number of references (such as U.S. Pat. No. 5,581,476, U.S. Pat. No. 5,214,132, U.S. Pat. No. 5,362,853, U.S. Pat. No. 4,904,584). These variant proteins have multiple amino acid substitutions, which have been designed to explore more stable, more active and more suitable forms of G-CSF for clinical use.

The commercially available recombinant human G-CSF needs to be injected frequently. It can be difficult to achieve a good clinical effect because of its poor bioavailability, short half-life in the human body, and vulnerability to proteases in vivo. Research has shown that the possibility of the proteins to become drugs is greatly increased when they are conjugated with polyethylene glycol (PEG). These "PEGylated" proteins have been fully applied in clinical practices (such as Katre, Advanced Drug Delivery Systems, 10:91 (1993); Inada; et. al.; J. Bioact and Compatible Polymers; 5:343 (1990)). Polyethylene glycol-protein conjugates have not only better physical and chemical stabilities, but also better resistance to protease enzymes in vivo. In addition, as the molecular weight of the conjugates increases, the half-life of the conjugates in vivo is extended. The toxicity will be reduced because of the lower possibility to produce antibodies in vivo and the reduced volume of distribution of the conjugates as comparing with original proteins.

PEG-modified G-CSF or G-CSF variant proteins have been disclosed in numerous references, such as EP0335423, EP0401384, U.S. Pat. No. 5,824,778, U.S. Pat. No. 5,985,265, WO0044785, WO2001051510, U.S. Pat. No. 5,824,784, etc. Specifically, among the PEG-G-CSF conjugates disclosed by U.S. Pat. No. 5,985,265, the conjugates modified at the N-terminus of G-CSF have the best biological activities both in vitro and in vivo. However, the selectivity of amino groups is poor when the modification with PEG is carried out through an acylation reaction, thus producing a mixture of G-CSF modified at various positions (amino group) by polyethylene glycol. Consequently, separations and purifications are required to obtain each monomer. The yield may be low and it can be difficult to manufacture on an industrial scale.

In U.S. Pat. No. 5,824,784, polyethylene glycol aldehydes with large molecular weights are used to modify G-CSF directly. With strict control of the pH of the reaction, relatively specific linking of the PEG to the N-terminus of protein can be achieved. However, the reaction with high selectivity uses the difference in the $pK_a$ of the side chain amino group and the $pK_a$ of the N-terminal amino group. This reaction is thus relatively difficult to control in manufacturing scales. In addition, because of the variable numbers of aldehyde groups in the polyethylene glycol aldehydes with large molecular weights in each batch, it is difficult to control the ratio between aldehydes and the proteins. Consequently, the reaction yields and production costs are difficult to control. Moreover, the different biological activities of the conjugates produced by coupling of aldehydes with different amino groups will affect the homogeneity and activity of the final product.

SUMMARY OF THE INVENTION

In view of the deficiencies of the prior art, one purpose of the present invention is to provide a G-CSF conjugate having a new structure of formula (I) and containing a water-soluble polymer, or pharmaceutically acceptable salts thereof. Another purpose of the present invention is to provide a method of preparing the conjugate of formula (I) or pharmaceutically acceptable salts thereof. Another purpose of the present invention is to provide a pharmaceutical composition containing such conjugates or pharmaceutically acceptable salts, and the use thereof.

The invention relates to a polymer-protein conjugate, or a pharmaceutically acceptable salt thereof, comprising a water-soluble polymer, a protein, and a linking group. The conjugate can be represented by formula (I):

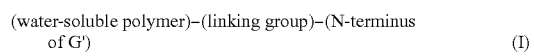
(water-soluble polymer)–(linking group)–(N-terminus of G')     (I)

The water-soluble polymer and the protein G' are linked together by a linking group attached to the N-terminus of the protein G'. The protein G' is selected from natural G-CSF, recombinant G-CSF and G-CSF analogues having the function of G-CSF. The water-soluble polymer is selected from the group consisting of polyethylene glycol, polypropylene glycol, polyacetic acid, and polyamino acid. Preferably, the polymer is polyethylene glycol (PEG). The molecular weight of PEG is preferably selected from 2 KD-100 KD. Preferably, the molecular weight of PEG is 5 KD-40 KD. PEG may be a linear or branched type. The linking group is preferably formed by a specific reaction between the functional group at the end of the water-soluble polymer and the functional group at the N-terminus of G'.

DESCRIPTION OF THE PREFERRED EMBODIMENTS

G' is selected from a natural G-CSF, a recombinant G-CSF, and gene mutation products with the function of G-CSF. Preferably, G' is the G-CSF derivatives set forth in SEQ ID NOs: 1-10. More preferably, G' is a naturally occurring human G-CSF sequence, or Met-G-CSF set forth in SEQ ID NO: 1.

Preferably, the chemical structure of the conjugates of formula (I) or pharmaceutically acceptable salts thereof is represented by formula (II):

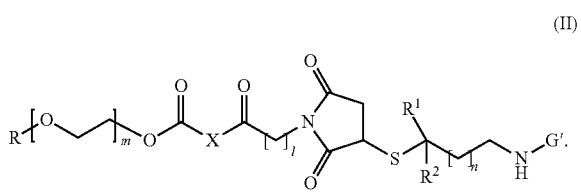

R is selected from $C_{1-4}$ linear or branched alkyl. Preferably, R is methyl or ethyl. More preferably, R is methyl. $R^1$ and $R^2$ are each independently selected from hydrogen or $C_{1-4}$ linear or branched alkyl. Preferably, $R^1$ and $R^2$ are independently hydrogen, methyl or ethyl. X is selected from O, S, NH,

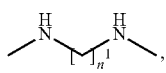

or

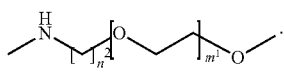

l is an integer selected from 1-20. Preferably, l is an integer selected from 1-10. More preferably, l is an integer selected from 1-5. m and $m_1$ are independently selected from an integer of 50-2500. Preferably, m and $m_1$ are independently selected from 100-1000. n, $n^1$ and $n^2$ are independently selected from 1-20. Preferably, n, $n^1$ and $n^2$ are independently selected from 1-10. More preferably, n, $n^1$ and $n^2$ are independently is an integer selected from 1-5. G' is selected from natural G-CSF, recombinant G-CSF or gene mutation products with the function of G-CSF.

Preferably, G' has a naturally occurring human G-CSF sequence.

Preferably, G' is Met-G-CSF (SEQ ID NO: 1).

Preferably, the conjugates of general formula (I) and (II) have formulae:

The conjugates of the formulae (I) and (II) can react with acids to form salts. The acids used are selected from organic acids or inorganic acids. The organic acid is selected from acetic acid, trifluoroacetic acid, propionic acid, butyric acid, maleic acid, p-toluenesulfonic acid, or combinations thereof. Preferably, the organic acid is acetic acid, or trifluoroacetic acid. Inorganic acid is selected from hydrochloric acid, sulfuric acid, phosphoric acid, methanesulfuric acid, or combinations thereof. Preferably, the inorganic acid is hydrochloric acid.

In the other aspect, this invention provides a method for preparing the conjugates of formulae (I) and (II), including the following steps:

1) reacting the compound of formula (III) with the N-terminal amino group of G' through a reductive amination to obtain the compound of formula (IV):

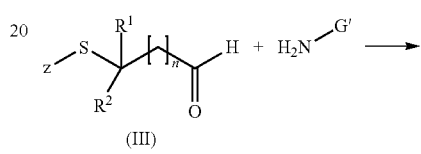

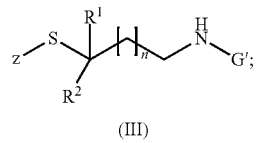

2) removing the protecting group of the thiol group from the compound of formula (IV) to obtain the compound of formula (V):

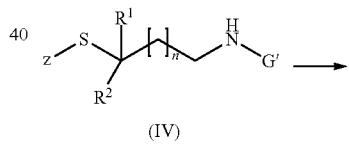

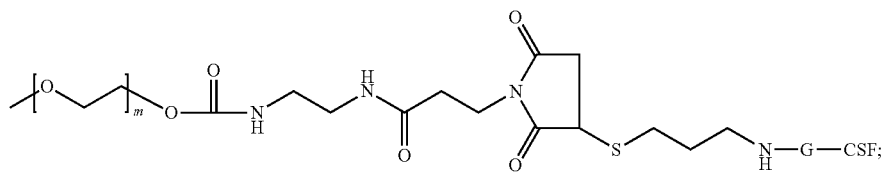

m is an integer selected from 400-500; and

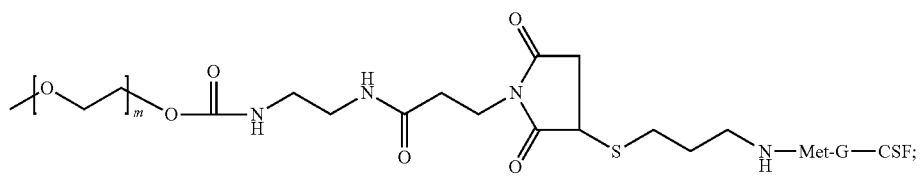

m is an integer selected from 400-500.

-continued

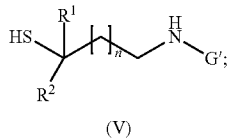

(V)

and 3) reacting the compound of formula (V) with mPEG-MAL (methoxy-PEG maleimide) through a Michael addition reaction to obtain the conjugate of formula (II):

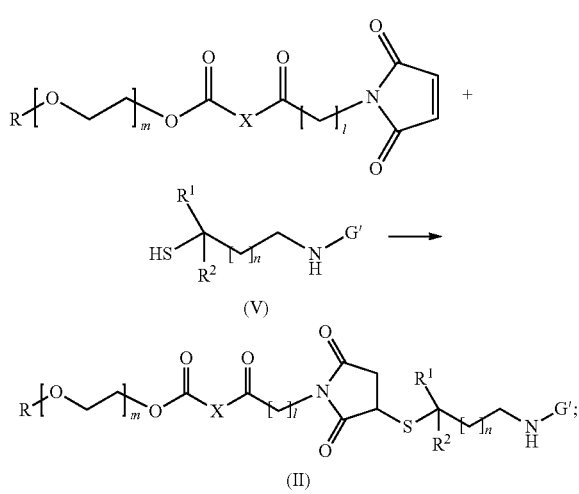

wherein:
R, $R^1$, $R^2$, G', X, l, m, and n are defined as above; and
z is a mercapto-protecting group selected from formyl, acetyl, propionyl, trityl, or tert-butyl group. Preferably, Z is acetyl group.

This invention also relates to the use of the conjugates or pharmaceutical salts thereof in the preparation of the medicaments treating leukopenia caused by radiotherapy or chemotherapy, AIDS and other immune deficiency diseases, and bacterial infections.

In the other aspect, this invention provides a pharmaceutical composition containing a pharmaceutically effective amount of the conjugate or a pharmaceutically acceptable salt thereof provided by this invention, and a pharmaceutically acceptable carrier.

This invention also relates to the use of the pharmaceutical compositions in the preparation of the medicaments treating leukopenia caused by radiotherapy or chemotherapy, AIDS and other immune deficiency diseases, and bacterial infections.

This invention discloses a new PEG-G-CSF conjugate and a new method for preparing thereof. Compared with traditional conjugates and the methods thereof, the following differences are present.

Firstly, the linking group between PEG and G-CSF can ensure specificity of the reaction at the N-terminus of the protein. Because the protein modified with small molecules at its N-terminus can be easily separated and purified, the specificity of the modified sites is ensured.

Secondly, because of the presence of the thiol group in the linking group, the control of pH of the reaction system will ensure the specificity of the Michael addition reaction.

In addition, because of the existence of the linking group, other functional groups, such as imido groups and ester groups, may also be introduced. These functional groups would assist the release of G-CSF from the conjugates in vivo.

Conjugates of the present invention or pharmaceutically acceptable salts thereof have a physiological activity of a natural human G-CSF, and have a longer in vivo circulating half-life and better granulocyte colony-stimulating activities than G-CSF.

Specifically, the structure of the conjugate disclosed by the present invention is shown as (II):

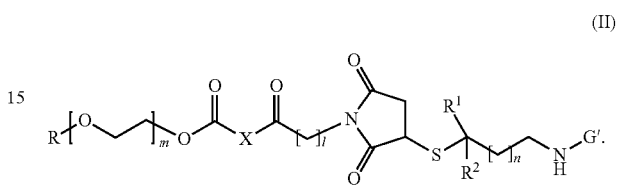

R is selected from $C_{1-4}$ linear or branched alkyl. Preferably, R is methyl or ethyl. More preferably, R is methyl. $R^1$ and $R^2$ are independently selected from hydrogen, or $C_{1-4}$ linear or branched alkyl. Preferably, $R^1$ and $R^2$ are independently hydrogen, methyl, or ethyl. X is selected from O, S, NH,

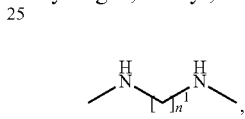

or

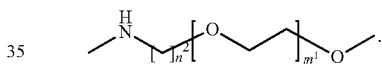

l is an integer selected from 1-20. Preferably, l is an integer selected from 1-10. More preferably, l is an integer selected from 1-5. m and $m_1$ are independently selected from an integer of 50-2500. Preferably, m and $m_1$ are independently selected from 100-1000. n, $n^1$ and $n^2$ are independently selected from 1-20. Preferably, n, $n^1$ and $n^2$ are independently is an integer selected from 1-5. G' is selected from natural G-CSF, recombinant G-CSF or gene mutation products with the function of G-CSF.

When X is O or S, the linking group contains an ester bond susceptible to hydrolysis by the esterase in vivo. After released from conjugates by hydrolysis, G-CSF in its free form can interact with the receptors to exhibit biological activities. When X is NH,

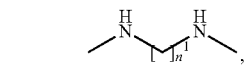

or

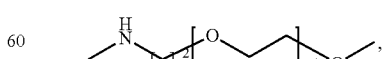

biological activities of the G-CSF are mainly achieved by the functions of the conjugates. Further, because the breaking of the imido bond through hydrolysis can release the free form of G-CSF in vivo, the possibility that the free G-CSF functions cannot be ruled out.

In the methods of preparation of the conjugates disclosed by the present invention, the intermediate (IV) is obtained by reacting the linking group containing a thiol group with the N-terminal amino group of G-CSF through a reductive amination. The linking group and the amino group of G-CSF can be connected by a variety of methods, such as reactions of various activated esters with amino groups. Because of the high selectivity of the reductive amination, the linking group is attached to the G-CSF by the reductive amination of the aldehyde group of the linking group and the N-terminal amino group of the G-CSF in the present invention. Reducing agent used in the present invention is selected from various reducing agents well-known in the art. Preferably, the reducing agent is sodium cyanoborohydride, or triacetoxy borohydride.

In the preparation of intermediate (V), corresponding reaction conditions are chosen according to various thiol-protecting groups. When the protecting group is trityl or tert-butyl, acidic conditions (such as trifluoroacetic acid, hydrochloric acid, methanesulfonic acid, etc.) are used to remove the protecting group. When the protecting group is acetyl, propionyl, etc., various methods and reagents that are well-known to the skilled person in the art are used to remove the protecting group. Preferably, hydroxylamine hydrochloride is used to remove the protecting group in pH 5-7.

In the preparation of the compound of formula (II), the pH of the reaction is controlled and the classical Michael addition is carried out. The reaction has a good selectivity up to more than 99%. After the reaction, the product can be separated and purified by reversed-phase high-performance liquid chromatography (RP-HPLC), ion exchange column, or gel column.

In the present invention, "$C_{1-4}$ alkyl" means linear or branched alkyl, such as methyl, ethyl, propyl, isopropyl, butyl group and so on.

In the present invention, preferably, G-CSF is a human G-CSF. The absence of variations in the sequence of the human G-CSF can reduce the antigenicity of the protein in vivo and maximally reduce the formation of neutralizing antibodies in vivo, thus enhancing drug efficacy. G-CSF and its variant proteins include, but are not limited to Met-G-CSF, Trp-G-CSF, Asp-G-CSF, and Glu-G-CSF, which are obtained by traditional methods of gene expression reported in the references. The preferred protein is Met-G-CSF expressed by E. coli. (for its sequence, see SEQ ID NO: 1).

The compound obtained by the present invention is administered in various dosage units. The dosage units can be expressed as the administered amount of the active compounds. In the pharmaceutical composition provided by the present invention, conjugates of formulae (I) and (II), or pharmaceutically acceptable salts thereof are active compounds. The pharmaceutical composition provided by the present invention can be used in adjuvant therapies for cancer patients subjected to chemotherapy or radiotherapy and for patients subjected to bone marrow transplantations, to prevent infections due to reduced immunity. It can also be used for treating chronic or relative leucopenia, acute myeloid leukemia, AIDS or other immune deficiency diseases, and fungal infections, especially infections by systemic or invasive candidiasis.

The administration dosage of the conjugates of formulae (I) and (II) or pharmaceutically acceptable salts thereof is 5-500 ug/kg. The unit of "ug" refers to the microgram of the conjugates of formulae (I) and (II) or pharmaceutically acceptable salts thereof. The unit of "kg" refers to the kilogram of the mammalian body weight. It is known that the administration dosage and frequency depend on many factors, such as the patient's sex, age, and type of diseases. Various formulations can be prepared by mixing the conjugates or the pharmaceutically accepted salts thereof provided by the present invention with conventional pharmaceutical carriers. The formulations can be administered to a patient by various ways, such as subcutaneous, intramuscular, and intravenous administrations.

EXAMPLES

Figure 1:
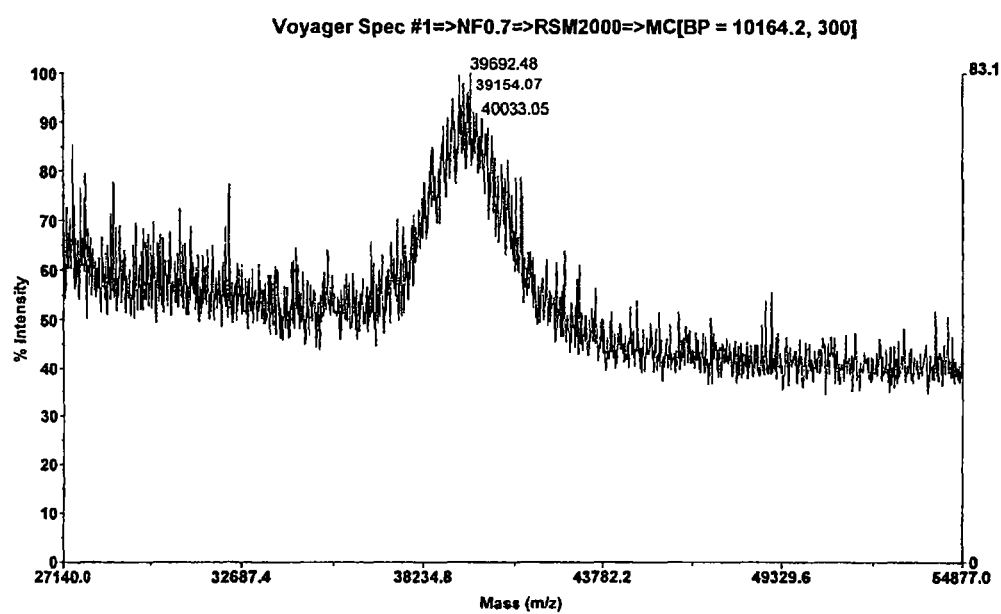
FIG. 1 shows a MALDI-TOF-TOF spectrum of compound 1 provided by the present invention.

For a more detailed description of the present invention, the following examples are provided. However, the scope of the present invention is not limited to these examples.

Example 1

| Reductive Amination of Met-G-CSF | |
| --- | --- |
| Met-G-CSF (pH = 5.0) | 40 mg/140 mL |
| [aldehyde structure: CH₃-C(=O)-S-CH₂-CH₂-C(=O)-H] | 7.0 mg |
| Sodium cyanoborohydride | 176 mg |

The original solution of Met-G-CSF was dialyzed against 0.1 M acetic acid/sodium acetate solution, from which 140 mL solution containing 40 mg proteins was taken out. An aldehyde with a small molecule (7.0 mg) was dissolved in acetonitrile (300 mL) to provide a solution. The aldehyde solution was added into the protein solution. Then sodium cyanoborohydride (176 mg) was added into the solution and the reaction was carried out for 3 hours at room temperature by stirring.

The reaction solution was dialyzed against 0.1 M of PBS solution (pH=6.2) containing 2 mM EDTA at 4° C.

Example 2

De-Protection of the Protecting-Group on the Thiol Group—Acetyl Group 10 mL of 0.1 M hydroxylamine hydrochloride (pH=6.3) was added into the protein solution prepared in Example 1 to make the concentration of hydroxylamine hydrochloride to 50 mM. The reaction was carried out under stirring for 30 minutes at room temperature to release the thiol group by removing acetyl group.

Example 3

Preparation of mPEG-Met-G-CSF (39 KD)

mPEG-MAL (400 mg, 20 KD) was added into the protein solution prepared by Example 2. The reaction was carried out under stirring for 60 minutes at room temperature. The purification was performed when HPLC showed the reaction was completed. The compound obtained was compound 1 of the present invention. The structure was confirmed by MALDI-TOF-TOF, shown in FIG. 1.

Column Conditions.

Column: Jupiter C4, 5u, 300 Å, 150*4.6.

Mobile phase: A: 0.05% TFA/H$_2$O; B: 0.05% TFA/CH$_3$CN.

| Gradient Conditions. | | | | |
|---|---|---|---|---|
| | 0' | 30' | 35' | 36' |
| A | 60% | 20% | 20% | 60% |
| B | 40% | 80% | 80% | 40% |

Conditions for Purification.

The column (1.6 cm×12 cm, the volume was about 24 mL, and flowing rate was 4 mL/minute) was filled with SP Sepharose HP.

Pre-treatment of the column: the column was washed with 5 times the volume of the column of 0.5 M NaOH solution. Then the column was washed to neutral pH with purified water. Finally, the column was equilibrated with 20 mM HAc/NaAc, pH4.0. The volume used to equilibrate the column was 5 times the volume of the column.

Loading the sample: the desalted sample was sucked into the column directly by a pump.

Elution: the column was eluted with 20 mM HAc/NaAc, pH 4.0. The volume of the eluent was 10 times the volume of the column to remove excessive PEG. Then the salt gradient from 0 to 50% was set with the running time of 50 minutes at 4 mL/minute. The impurities, products and unreacted proteins were eluted and collected successively.

Example 4

Preparation of mPEG-Met-G-CSF (59 KD)

Figure 2:
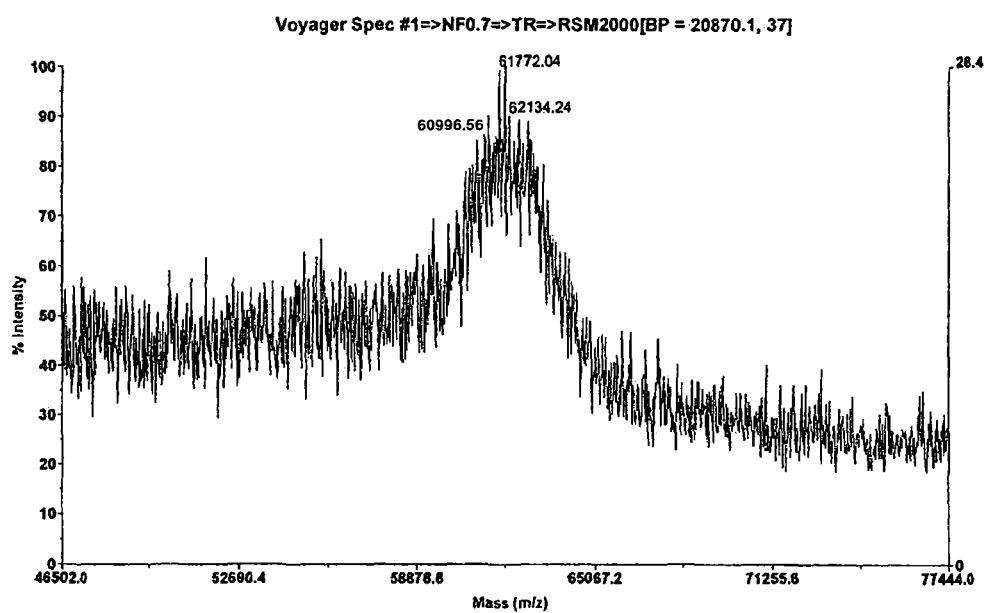
FIG. 2 shows a MALDI-TOF-TOF spectrum of compound 2 provided by the present invention.

The method of preparation and purification is the same as in Example 3, except that mPEG-MAL (400 mg, 20 KD) was replaced with mPEG-MAL (800 mg, 40 KD). The compound obtained is compound 2 of the present invention. Its MALDI-TOF-TOF spectrum is shown in FIG. 2.

Example 5

Preparation of the Injectable Solution of mPEG-Met-G-CSF (39 KD), i.e. Compound 1

| | |
|---|---|
| Sodium acetate: | 0.12 g. |
| Polysorbate 20: | 35 mg. |
| Sorbitol: | 50 g. |
| Compound 1: | 10 g. |

In an aseptic room, sodium acetate (0.12 g), polysorbate 20 (35 mg), and sorbitol (50 g) were weighted and dissolved in injectable water (1000 mL) under stirring. Compound 1 (10 g) was added to the solution. The mixture was stirred to form a homogeneous solution. The injectable water was added to the solution to make a final volume of 3000 mL. After filtered with 0.22 μm microporous membrane, the solution was packaged and sealed with sterilized stoppers.

Test 1

The Comparison of the Effects of PEG-G-CSF and G-CSF on the Increase of the Peripheral White Blood Cell Count Note: PEG-G-CSF refers to compound 1 of the present invention.

1. Purpose of the Test

The purpose is to evaluate and compare the effects of PEG-G-CSF and G-CSF on the increase of the peripheral white blood cell count in the mice treated by cyclophosphamide.

2. Materials and Methods

PEG-G-CSF, G-CSF and cyclophosphamide (CTX) were provided by Jiangsu Hansoh Pharmaceutical Co., Ltd. The solutions of the compounds were diluted with saline before using.

Female Kunming mice were purchased from Shanghai Experimental Animal Center of Chinese Academy of Sciences, weighting 18-22 g with the number of 10 in each group.

After the mice were adapted to the environment, cyclophosphamide was administered by intraperitoneal injections. PEG-G-CSF and G-CSF were administered by subcutaneous injections the next day. PEG-G-CSF was subcutaneously injected once at 0.5, and 1.0 mg/kg, respectively. G-CSF was subcutaneously injected once per day for 4 consecutive days with the dosage of 0.1, 0.2 mg/kg, respectively. After the administrations of PEG-G-CSF and G-CSF, the mice were sacrificed by cervical dislocation. The blood cells were counted with an ABC automatic blood cell counter.

3. Results

Figure 3:
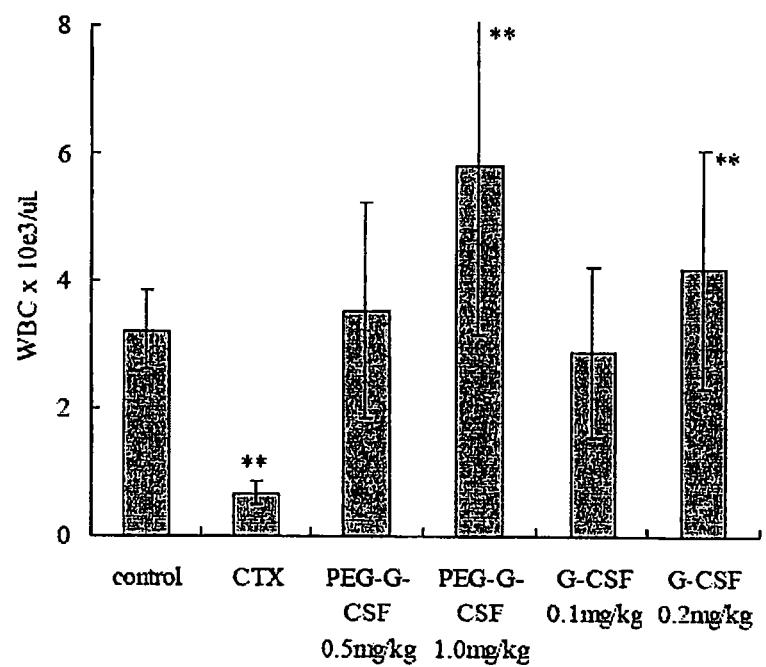
FIG. 3 shows the effects of PEG-G-CSF and G-CSF on the peripheral white blood cell count of mice treated by cyclophosphamide.

The intraperitoneal injection of CTX significantly decreases counting for peripheral white blood cell, blood erythrocyte, and platelet (average P<0.01, compared with the control, shown in FIGS. 3-5), indicating that CTX strongly inhibits functions of the bone marrow.

A single subcutaneous injection of PEG-G-CSF to the mice treated by cyclophosphamide increases the peripheral white blood cell count. When 0.5 mg/kg is administered, the white blood cell count returns to the normal level. When 1.0 mg/kg is administered, the peripheral white blood cell count is even higher than the normal level (P<0.01, compared with the control, FIG. 3). However, PEG-G-CSF has no obvious effect on the increasing of the peripheral blood erythrocyte count or platelet count (FIGS. 4 and 3), indicating that the effect of PEG-G-CSF is specific.

Figure 4:
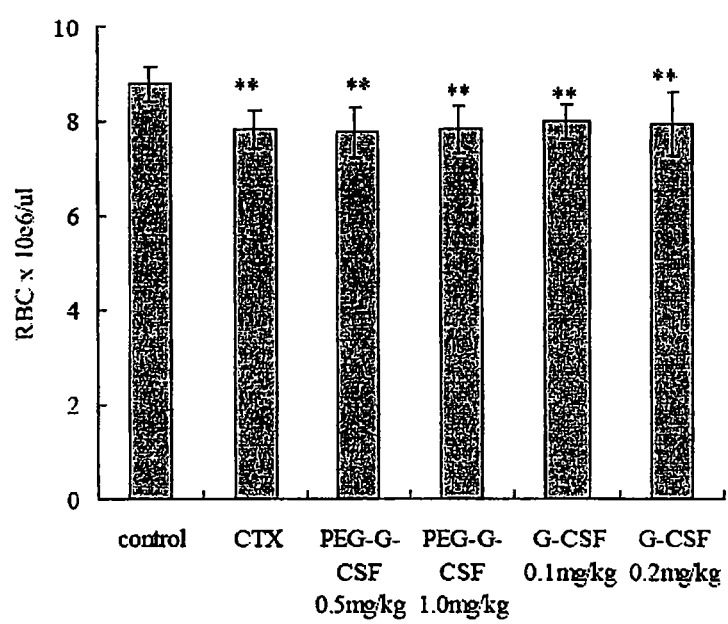
FIG. 4 shows the effects of PEG-G-CSF and G-CSF on the peripheral blood erythrocyte count of mice treated by cyclophosphamide.
Figure 5:
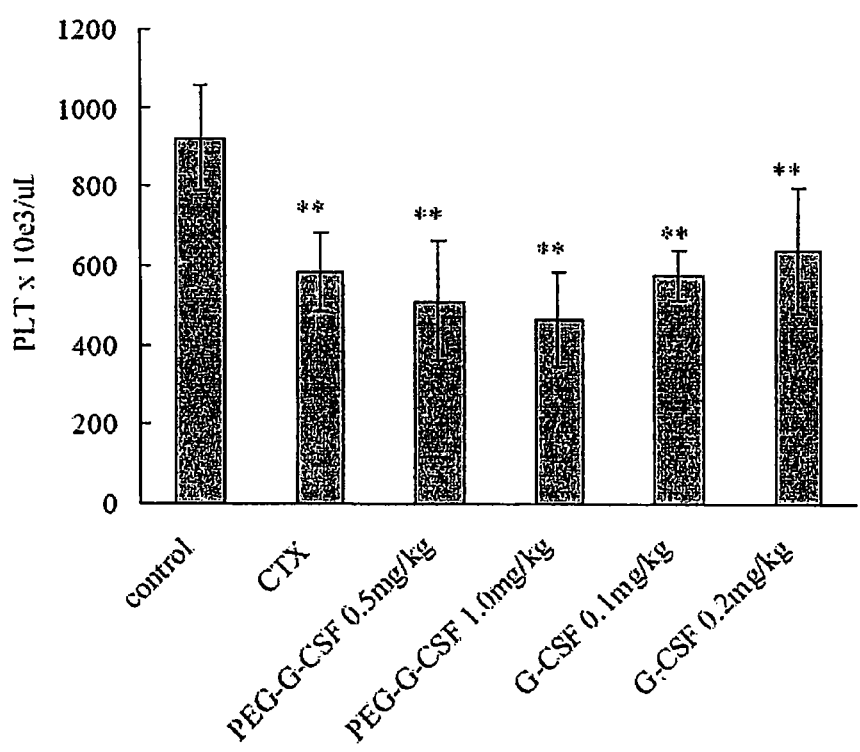
FIG. 5 shows the effects of PEG-G-CSF and G-CSF on the peripheral blood platelet count of mice treated by cyclophosphamide.

The continuous subcutaneous injection of G-CSF to the mice treated by cyclophosphamide also increases the peripheral white blood cell count. When 0.1 mg/kg is administered, the white blood cell count rises to the normal level. When 0.2 mg/kg is administered, the white blood cell count is higher than the normal level (P<0.01, compared with the control, FIG. 3), indicating an obvious dose dependency. However, G-CSF has no significant effect on the peripheral blood erythrocyte and platelet count (FIGS. 4 and 5).

According to the results, where the total amounts of PEG-G-CSF and G-CSF administered are similar, the single subcutaneous injection of PEG-G-CSF and multiple subcutaneous injections of G-CSF have equivalent efficacy on the peripheral blood white blood cell count of the mice.

4. Conclusions

Both PEG-G-CSF and G-CSF significantly increase the peripheral blood white blood cell count of the mice treated with cyclophosphamide. In the cases where the total amount administered is similar, the single subcutaneous injection of compound 1 of the present invention and multiple subcutaneous injections of G-CSF have equivalent efficacy on the peripheral blood white blood cell count of the mice.

The invention claimed is:

1. A polymer-protein conjugate, or a pharmaceutically acceptable salt thereof, comprising a water-soluble polymer, a protein, and a linking group; wherein
the water-soluble polymer is selected from the group consisting of polyethylene glycol, polypropylene glycol, polyacetic acid, and polyamino acid;
the protein is selected from natural granulocyte colony stimulating factor [G-CSF], recombinant G-CSF and G-CSF analogues having the function of G-CSF; and
the water-soluble polymer and the protein are linked together by a linking group; and
wherein the linking group is attached to the N-terminus of the protein through an amine bond, and the linking group comprises a sulfur atom.

2. The conjugate of claim 1, or a pharmaceutically acceptable salt thereof, wherein the water-soluble polymer is polyethylene glycol (PEG).

3. The conjugate of claim 2, or a pharmaceutically acceptable salt thereof, wherein the PEG has a molecular weight of about 2 kilodaltons to about 100 kilodaltons.

4. The conjugate of claim 3, or a pharmaceutically acceptable salt thereof, wherein the PEG has a molecular weight of about 5 kilodaltons to about 40 kilodaltons.

5. The conjugate of claim 1, or a pharmaceutically acceptable salt thereof, wherein the G-CSF analogue has the sequence selected from any one of SEQ ID NOs: 1-10.

6. The conjugate of claim 5, or a pharmaceutically acceptable salt thereof, wherein the G-CSF analogue has the sequence of SEQ ID NO: 1.

7. The conjugate of claim 1, or a pharmaceutically acceptable salt thereof, wherein G-CSF is a naturally occurring human G-CSF sequence.

8. The conjugate of claim 1, which is a pharmaceutically acceptable salt, wherein the salt is selected from the group consisting of a hydrochloride salt, a sulfate salt, a phosphate salt, a methanesulfonate salt, an acetate salt, a trifluoroacetate salt, a propionate salt, a butyrate salt, a maleate salt, a p-toluenesulfonate salt, and combinations thereof.

9. A method for treatment of leucopenia caused by radiotherapy or chemotherapy, AIDS and other immune deficiency diseases, and bacterial infections, comprising administering to a patient in need thereof a therapeutically effective amount of the conjugate of claim 1, or a pharmaceutically acceptable salt thereof.

10. A pharmaceutical composition, which comprises a pharmaceutically effective amount of the conjugate of claim 1, or a pharmaceutically acceptable salt thereof, and a pharmaceutically acceptable carrier.

11. A method for treatment of leucopenia caused by radiotherapy or chemotherapy, AIDS and other immune deficiency diseases, and bacterial infections, comprising administering to a patient in need thereof a therapeutically effective amount of the composition of claim 10.

12. The conjugate of claim 1, or a pharmaceutically acceptable salt thereof, wherein the linking group is

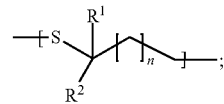

wherein $R^1$ and $R^2$ are each independently selected from hydrogen and $C_{1-4}$ linear or branched alkyl; and wherein n is an integer of from 1-20.

13. The conjugate of claim 12, or a pharmaceutically acceptable salt thereof, wherein $R^1$ and $R^2$ are independently selected from the group consisting of hydrogen, methyl and ethyl.

14. The conjugate of claim 12, or a pharmaceutically acceptable salt thereof, wherein $R^1$ is hydrogen.

15. The conjugate of claim 12, or a pharmaceutically acceptable salt thereof, wherein $R^2$ is hydrogen.

16. The conjugate of claim 12, or a pharmaceutically acceptable salt thereof, wherein n is an integer of from 1-10.

17. The conjugate of claim 16, or a pharmaceutically acceptable salt thereof, wherein n is an integer of from 1-5.

18. The conjugate of claim 3, or a pharmaceutically acceptable salt thereof, wherein G' has the sequence of SEQ ID NO: 2.

19. The conjugate of claim 1, or a pharmaceutically acceptable salt thereof, wherein G-CSF has the sequence of SEQ ID NO: 2.

20. A polymer-protein conjugate, or a pharmaceutically acceptable salt thereof, which has formula (II):

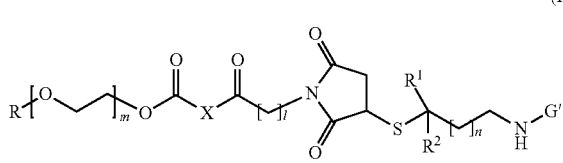

(II)

wherein:
R is selected from $C_{1-4}$ linear and branched alkyl;
$R^1$ and $R^2$ are each independently selected from hydrogen, and $C_{1-4}$ linear and branched alkyl;
X is selected from O, S, NH,

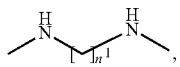, and

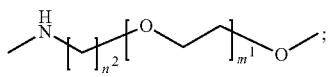;

l is an integer selected from 1-20;
m and $m^1$ are independently selected from an integer of 50-2500;

n, $n^1$ and $n^2$ are independently selected from an integer of 1-20; and
G' is selected from natural G-CSF, recombinant G-CSF and G-CSF analogues having the function of G-CSF.

21. The conjugate of claim 20, or a pharmaceutically acceptable salt thereof, wherein R is methyl or ethyl.

22. The conjugate of claim 20, or a pharmaceutically acceptable salt thereof, wherein $R^1$ and $R^2$ are independently selected from the group consisting of hydrogen, methyl and ethyl.

23. The conjugate of claim 20, or a pharmaceutically acceptable salt thereof, wherein $R^1$ is hydrogen.

24. The conjugate of claim 20, or a pharmaceutically acceptable salt thereof, wherein $R^2$ is hydrogen.

25. The conjugate of claim 20, or a pharmaceutically acceptable salt thereof, wherein n is selected from an integer of from 1 to 10.

26. The conjugate of claim 25, or a pharmaceutically acceptable salt thereof, wherein n is selected from an integer of from 1 to 5.

27. The conjugate of claim 25, or a pharmaceutically acceptable salt thereof, wherein n is 1.

28. The conjugate of claim 20, or a pharmaceutically acceptable salt thereof, wherein m is selected from an integer of from 100 to 1000.

29. The conjugate of claim 20, or a pharmaceutically acceptable salt thereof, wherein l is an integer of from 1 to 10.

30. The conjugate of claim 20, or a pharmaceutically acceptable salt thereof, wherein l is an integer of from 1 to 5.

31. The conjugate of claim 20, or a pharmaceutically acceptable salt thereof, wherein l is 2.

32. The conjugate of claim 20, or a pharmaceutically acceptable salt thereof, wherein X is

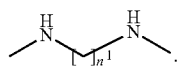.

33. The conjugate of claim 32, or a pharmaceutically acceptable salt thereof, wherein $n^1$ is selected from an integer of from 1 to 10.

34. The conjugate of claim 33, or a pharmaceutically acceptable salt thereof, wherein $n^1$ is 2.

35. A conjugate or a pharmaceutically acceptable salt thereof, wherein the conjugate is selected from:

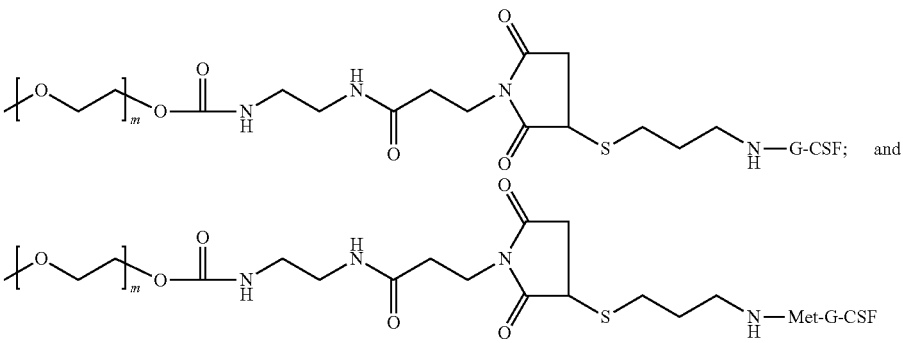

m is an integer selected from 400-500.